United States Patent [19]

Strickler et al.

[11] Patent Number: 5,679,814

[45] Date of Patent: Oct. 21, 1997

[54] PURIFICATION OF METALLOCENES

[75] Inventors: Jamie R. Strickler; John M. Power, both of Baton Rouge, La.

[73] Assignee: Albemarle Corporation, Richmond, Va.

[21] Appl. No.: 570,031

[22] Filed: Dec. 11, 1995

[51] Int. Cl.$^6$ .................. C07F 7/08; C07F 17/00; C07F 17/02

[52] U.S. Cl. .................. 556/11; 556/43; 556/143; 534/11; 534/15

[58] Field of Search .................. 556/11, 43, 143; 534/11, 15

[56] References Cited

U.S. PATENT DOCUMENTS

| | | | |
|---|---|---|---|
| 4,528,408 | 7/1985 | Plummer | 568/808 |
| 4,794,096 | 12/1988 | Ewen | 502/117 |
| 4,892,851 | 1/1990 | Ewen et al. | 502/104 |
| 4,931,417 | 6/1990 | Miya et al. | 502/117 |
| 5,017,714 | 5/1991 | Welborn, Jr. | 556/12 |
| 5,036,034 | 7/1991 | Ewen | 502/117 |
| 5,075,467 | 12/1991 | Desobry | 556/53 |
| 5,103,030 | 4/1992 | Rohrmann et al. | 556/12 |
| 5,120,867 | 6/1992 | Welborn, Jr. | 556/12 |
| 5,145,819 | 9/1992 | Winter et al. | 502/117 |
| 5,276,208 | 1/1994 | Winter et al. | 556/53 |
| 5,296,434 | 3/1994 | Karl et al. | 502/117 |
| 5,314,973 | 5/1994 | Welborn, Jr. | 526/126 |
| 5,324,800 | 6/1994 | Welborn, Jr. et al. | 526/160 |
| 5,329,033 | 7/1994 | Spaleck et al. | 556/53 |
| 5,340,701 | 8/1994 | Desobry | 430/325 |
| 5,441,920 | 8/1995 | Welborn, Jr. | 502/103 |
| 5,455,365 | 10/1995 | Winter et al. | 556/7 |
| 5,455,366 | 10/1995 | Rohrmann et al. | 556/8 |
| 5,512,693 | 4/1996 | Rosen et al. | 556/11 X |
| 5,523,435 | 6/1996 | Lisowsky | 556/11 |
| 5,532,396 | 7/1996 | Winter | 556/11 |
| 5,541,350 | 7/1996 | Murata et al. | 556/11 X |
| 5,556,997 | 9/1996 | Strickler et al. | 556/11 |
| 5,569,746 | 10/1996 | Lee et al. | 534/11 |
| 5,585,508 | 12/1996 | Kuber et al. | 556/11 |

FOREIGN PATENT DOCUMENTS

| | | |
|---|---|---|
| 2055218 | 5/1992 | Canada. |
| 2084016 | 5/1993 | Canada. |
| 0530908 | 3/1993 | European Pat. Off.. |
| 0581754 | 2/1994 | European Pat. Off.. |
| 4434640 | 2/1996 | Germany. |
| 646438 | 11/1984 | Switzerland. |

OTHER PUBLICATIONS

Ray and Westland: "The Infrared Spectra of Some Compounds of Zirconium(IV) and Hafnium(IV) Tetrahalides and Ligands Containing Group V Donor Atoms"; inorganic Chemistry, vol. 4, No. 10, Oct. 1965, pp. 1501–1504.

Spaleck, et al., The Influence of Aromatic Substituents on the Polymerization Behavior of Bridged Zirconocene Catalysts; Organometallics, vol. 13, No. 3, 1994, pp. 954–963.

Spaleck, et al., "High Molecular Weight Polypropylene through Specifically Designed Zirconocene Catalysts"; Angew Chem. Int. Ed. Engl, 1992, vol. 31, No. 10, pp. 1347–1350.

Jordan, et al., "Synthesis and Structures of Neutral and Cationic rac–(Ethylenebis(tetrahydroindenyl)) zirconium(IV) Benzyl Complexes"; Organometallics, vol. 9, No. 5, 1990, pp. 1539–1545.

Samuel et al; "π–Cyclopentadienyl and π–Indenyl Compounds of Titanium, Zirconium, and Hafnium Containing σ–Bonded Organic Substituents"; Journal of the American Chemical Society, 1973, 95:19; pp. 6263–6267.

The Metallocene Monitor, Special Feature; Exxon, Hoechst, and BASF All Have Parts of Metallocene–Catalyzed Isotactic PP; pp. 4–10; (undated).

Stehling, et al., "ansa–Zirconocene Polymerization Catalysts with Annelated Ring Ligands–Effects on Catalytic Activity and Polymer Chain Length" Organometallics, 1994 vol. 13, No. 3, pp. 964–970.

*Primary Examiner*—Paul F. Shaver
*Attorney, Agent, or Firm*—Philip M. Pippenger

[57] ABSTRACT

Metallocenes, such as silicon bridged ansa-metallocenes, are purified by heating a slurry of the metallocene at elevated temperature in an aprotic, polar solvent so as to extract impurities from the metallocene into the solvent and then separating the impurity containing solvent from the metallocene.

11 Claims, No Drawings

PURIFICATION OF METALLOCENES

This invention relates generally to the purification of metallocenes and more specifically to a process of removing contaminants from bridged metallocenes which are unstable in the presence of protic solvents and chlorinated hydrocarbons.

Metallocenes are useful in catalyzing olefin polymerization. Metallocenes prepared by salt elimination typically contain unwanted side products such as LiCl, transition metal halides, residual solvent complexed impurities and metallocene oligomers. Many metallocenes are not very soluble in hydrocarbon solvents and typically require the use of chlorinated hydrocarbon solvents to obtain even the modest solubilities needed for purification by extraction and recrystallization techniques. Some bridged or ansa-metallocenes are relatively unstable and decompose not only in protic solvents such as water, methanol and secondary amines but even in chlorinated hydrocarbons. This makes the removal of unwanted impurities, which can adversely impact the polymerization catalyst activity of the metallocene, difficult and costly.

A metallocene purification process has now been found which is fast, economical, reproducible and avoids metallocene decomposition or other excessive losses of product.

In accordance with this invention there is provided a process for the purification of a metallocene, which process comprises refluxing a slurry of metallocene in an aprotic, polar solvent so as to extract impurities from said metallocene into said solvent and separating the impurity containing solvent from said metallocene.

Surprisingly, the metallocene is stable even after prolonged heating at reflux temperatures in the aprotic, polar solvents. This heating provides relatively rapid and effective purification compared to the prolonged contact with such solvents at ambient temperature required to achieve less effective impurity removal.

Metallocenes, when used in combination with co-catalysts such as aluminoxanes, boranes and/or borates are highly active single-site catalysts for olefin polymerization and co-polymerization. The metallocenes can be prepared by reacting a deprotonated ligand, which contains at least one cyclopentadienyl or a related group based on cyclopentadienyl such as indenyl or fluorenyl, with a transition, lanthanide or actinide metal compound, such as a metal halide, or by reacting the ligand with a metal amide. The metallocene product of this metallation reaction may contain both inorganic and organic impurities which, if not removed, can interfere with the activity and efficiency of metallocene when used for single-site catalysis in a gas-phase or slurry phase process.

Metallocene catalyst compounds which can be purified by the process of the invention are organometallic compounds of transition, and especially Group 3, 4, 5 and 6 metals, lanthanide metals and actinide metals. Non-limiting examples of such metals include Y, Ti, Zr, Hf, V, Ta, Ce, Th, U and Cr and the like which have limited solubility in aprotic polar solvents. As used herein the term "metallocene" includes derivatives of the metals which contain at least one cyclopentadienyl type moiety. The compounds can be described as metallocene (or bent metallocene in the case of bis-cyclopentadienyl type derivatives) with ancillary anionic ligands or hydrocarbyl carbyl groups. For example, one such group of metallocenes can be represented by the general formula $Z_t(\eta^5—R'_nH_mC_5)_sMX_{r-s}$, where R' is a carbon or carbon and heteroatom (N, O, S, P, B, Si and the like) containing group such as $C_1$ to $C_{20}$ alkyl, $C_3$ to $C_2$ cycloalkyl, $C_7$ to $C_{20}$ aralkyl or $C_6$ to $C_{14}$ aryl. Non-limiting examples of such R' groups include methyl, ethyl, trimethylsilyl, t-butyl, cyclohexyl, phenyl, 4-methylphenyl, 2,4,6-trimethylphenyl, 2-phenylethyl and the like. The R' substituents can be different in type and in number on each cyclopentadienyl ring and can form fused cyclic groups attached to the rings, such as indenyl, fluorenyl and further substituted derivatives thereof. Z is a bridging group between rings such as silane, phosphine, amine or carbon groups, t is 0 or 1, m and n are integers of 0 to 5, m+n+t=5, r is equal to the oxidation state of the metal, s is 1 or 2 when r=3 and s is 1 to 3 when r=4, M is a transition, lathanide or actinide metal and X is halogen or psuedohalogen (e.g. a leaving group in nucleophilic substitution such as ester, alkoxide, cyanide, tosylate, triflate, β-diketonate and the like), hydride or $C_l$ to $C_8$ alkyl or aryl.

Such metallocenes and other types are described, for example, in U.S. Pat. Nos. 2,864,843; 2,983,740; 4,665,046; 4,874,880; 4,892,851; 4,931,417; 4,952,713; 5,017,714; 5,026,798; 5,036,034; 5,064,802; 5,081,231; 5,145,819; 5,162,278; 5,245,019; 5,268,495; 5,276,208; 5,304,523; 5,324,800; 5,329,031; 5,329,033; 5,330,948, 5,347,025; 5,347,026; and 5,347,752, whose teachings with respect to such metallocenes are incorporated herein by reference.

Specific, non-limiting examples of metallocenes include racemic and meso dimethylsilanylene-bis (methylcyclopentadienyl)-hafnium dichloride, racemic dimethylsilanylene-bis(indenyl)-zirconium dichloride, racemic ethylene-bis-(indenyl)zirconium dichloride, racemic dimethylsilanylene-bis-(indenyl)thorium dichloride, racemic dimethylsilanylene-bis(4,7-dimethyl-1-indenyl) zirconium dichloride, racemic dimethylsilanylene-bis (indenyl)uranium dichloride, racemic dimethylsilanylene-bis(2,3,5-trimethyl-1-cyclopentadienyl)zirconium dichloride, racemic dimethylsilanylene(3-methyl-cyclopentadienyl)hafnium dichloride, racemic dimethyl-silanylene-bis(1-(2-methyl-4-ethylindenyl zirconium dichloride; racemic dimethylsilanylene-bis(2-methyl-4,5,6, 7-tetrahydro-1-indenyl)zirconium dichloride, (tert-butylamide)dimethyl(tetramethyl-$\eta^5$-cyclopentadienyl) silanetitanium dichloride, (tert-butylamide)dimethyl (tetramethyl-$\eta^5$-cyclopentadienyl)silanechromium dichloride, (tert-butylamide)dimethyl(-$\eta^5$-cyclopentadienyl)silanetitanium dichloride, (tert-butylamide)dimethyl(tetramethyl-$\eta^5$-cyclopentadienyl) silanemethyltitanium bromide, (tert-butylamide) (tetramethyl-$\eta^5$-cyclopentadienyl)-1,2-ethanediyluranium dichloride, (tert-butylamide)(tetramethyl-$\eta^5$-cyclopentadienyl)-1,2-ethanediyltitanium dichloride, (methylamido)-(tetramethyl-$\eta^5$-cyclopentadienyl)-1,2-ethanediylcerium dichloride, (methylamido)(tetramethyl-$\eta^5$-cyclopentadienyl)-1,2-ethanediyltitanium dichloride, (ethylamido)(tetramethyl-$\eta^5$-cyclopentadienyl) methylenetitanium dichloride, (tert-butylamide)dibenzyl (tetramethyl-$\eta^5$-cyclopentadienyl)silanebenzylvanadium chloride, (benzylamido)dimethyl(indenyl)silanetitanium dichloride, (phenylphosphido)dimethyl-(tetramethyl-$\eta^5$-cyclopentadienyl)silanebenzyltitanium chloride, rac-dimethylsilyl(2-methyl-1-indenyl)$_2$zirconium dichloride, rac-ethylene(2-methyl-1-indenyl)$_2$zirconium dichloride, rac-dimethylsilyl(2-methyl-1-indenyl)$_2$dimethylzirconium and rac-ethylene(2-methyl-1-indenyl)$_2$dimethylzirconium.

The metallocenes can be prepared as known in the art by, for example, reacting the appropriate ligand with a deprotonating agent such as an alkali metal, an alkali metal alkyl, or a Grignard reagent and then reacting the resulting ligand salt with the transition, lanthanide or actinide metal compound. Suitable deprotonating agents include, for example, Li metal, Na powder, RLi, NaH, LiH, KH or a Grignard reagent (RMgX, where R is $C_1$ to $C_{10}$ hydrocarbyl and X is halogen). Preferred are alkyllithium compounds such as methyllithium, n-butyllithium, s-butyllithium, t-butyllithium, phenyl-lithium, and the like.

Usually, the deprotonating agent contained in a hydrocarbon solvent such as hexanes, cyclohexane, heptane, pentane, toluene and the like, is added to an acyclic or cyclic ether solution of the ligand. Alternatively, the deprotonating agent in hexanes or a mixture of hexanes and toluene can be added to the dry ligand, with diethyl ether or THF being added, if necessary, to provide a thinner, more workable solution.

The metal compound is usually used in the form of its ether or THF complex; although it can be used directly as a metal halide. The ligand salt need not be recovered from the deprotonation reaction mixture prior to the metallization reaction and can be added to the metal compound or vice versa.

The metal compound such as a metal halide may contain impurities and is usually used in about a 10% stoichiometric excess to provide sufficient metal to react with the deprotonated ligand. The excess metal compound and impurities will be carried over into the crude metallocene product. Common impurities in the metal compounds are metal oxides which must be removed because the presence of oxygen in the catalyst can effect its performance as a single-site catalyst. The crude metallocenes also may contain residual solvent, such as THF, which cannot be removed by evaporation techniques, probably because it is complexed with another impurity. The process of the invention significantly reduces these impurities and especially the metal halide and residual solvent impurities.

The solvents used to treat the metallocene are aprotic polar solvents of low acidity in which the metallocene is no more than sparingly soluble at ambient temperatures (less than about 2 percent by weight) but which are solvents for metal salts such as LiCl and $ZrC_4$. The solvent should also be inert with respect to the metallocene. Non-limiting examples of such solvents include tetrahydrofuran (THF), acetone, pyridine and the like. The amount of solvent is selected to obtain the maximum removal of impurity with the minimum loss of product for the particular metallocene. In general, amounts of from about 5 to 10 ml of solvent per gram of metallocene are used.

The mixture of solvent and metallocene are heated at elevated temperature, e.g. at least about 40° C. and, typically, at reflux temperature for from about 30 minutes to 5 hours. Longer times of 20 hours or more can be used, if necessary, without causing metallocene degradation. The solvent containing the impurities is then separated from the metallocene by any conventional solid-liquid separation technique such as filtering, centrifugation and/or recantation after cooling to ambient temperature. The product metallocene is then washed with fresh solvent and dried.

The invention is further illustrated by, but is not intended to be limited to, the following examples.

EXAMPLES 1–5

Impure dimethylsilylbis(2-methyl-1-indenyl)zirconium dichloride which contained a mixture of 90.6 mole percent racemic isomers and 9.4 mole percent meso isomer along with THF-containing impurity (9 mole percent) and 10–15 wt. percent of mostly salt (LiCl, $ZrCl_4$) impurities was slurried in from 5 to 16 ml of THF/gram of crude metallocene and refluxed for 2 to 17 hours. After cooling the slurry to ambient temperature, the metallocene was isolated and dried. Samples were prepared in $CDCl_3$ (dried over activated basic alumina) for $^1H$ NMR analysis. The purification conditions, yield and THF impurity data are listed in Table I. The results of wet chemical analysis for zirconium, lithium and chloride are given in Table II.

TABLE I

Process Conditions and $^1H$ NMR Results

| Example | THF/ Metallocene (mL/g) | Temp. °C. | Time (h) | Yield (wt. %) | Rac (mol %) | Meso (mol %) | THF (mol %) |
|---|---|---|---|---|---|---|---|
| 1 | 10 | 67 | 2 | 63 | 98 | 2 | 4 |
| 2 | 10 | 67 | 17 | 63 | 98 | 2 | 2 |
| Comp. 1 | 10 | 25 | 24 | 65 | 98 | 2 | 6 |
| Comp. 2 | 10 | 60 | wash | 74 | 94.5 | 5.5 | 9 |
| 3 | 5 | 67 | 2 | 70 | 98 | 2 | 7.5 |
| 4 | 7 | 67 | 5 | 65 | 99 | 1 | 3 |
| 5 | 16 | 67 | 3 | 55 | 98 | 2 | 3.5 |

TABLE II

Wet Chemical Analyses Results

| Example | Zirconium (%) | Lithium (ppm) | Chloride (%) |
|---|---|---|---|
| Theoretical | 19.14 | 0 | 14.88 |
| Impure Metallocene | 16.3 | 25,000 | 26.2 |
| 1 | 20.1 | 196 | 14.9 |
| Comparison 1 | 19.7 | 230 | 14.6 |
| Comparison 2 | 18.6 | 11,200 | 19.5 |
| 3 | 19.9 | 1260 | 15.3 |
| 4 | 19.6 | 188 | 14.9 |

According to the results of Examples 1 and 3–5 shown in the tables, the mount of solvent used should be sufficient to achieve good impurity removal with a minimum loss of product as demonstrated by Examples 1 and 4 where 10 and 7 ml solvent/gram of product were used. Example 3 which used 5 ml/gram of product gave a higher yield but of less pure material. Example 5 which used 16 ml/gram of product resulted in a lower yield of product. Example 1 achieved good impurity removal in only 2 hours at reflux and, as demonstrated in Example 2, the product was stable even when heated at reflux for 17 hours which further reduced the THF-containing impurity down to 2 mole percent. Comparison 1 at room temperature achieved good inorganic impurity removal after 24 hours but the THF containing impurity remained high. A wash of product at 60° C. removed only about half of the inorganic impurities and little if any of the THF impurity. Also, a significant amount of metallocene product was dissolved. The process of the invention also has the advantage of removing meso-isomer to provide a mostly racemic-metallocene for catalyst use.

What is claimed is:

1. A process for the purification of impure metallocene that contains at least a tetrahydrofuran-containing impurity, which process comprises heating a slurry of said metallocene at elevated temperature in an aprotic, polar solvent selected from the group consisting of ethers, ketones, and tertiary amines, the temperature and duration of the heating and the amount of solvent relative to said metallocene being sufficient to extract impurities including tetrahydrofuran-containing impurity from said metallocene into said solvent; and then separating the impurity-containing solvent from said metallocene.

2. The process of claim 1 wherein said aprotic, polar solvent is tetrahydrofuran.

3. The process of claim 1 wherein said metallocene is an ansa-metallocene.

4. The process of claim 3 wherein said ansa-metallocene is a silicon bridged bis(2-methyl-1-indenyl) ligand-containing metallocene.

5. The process of claim 4 wherein said ansa-metallocene is dimethylsilylbis(2-methyl-1-indenyl)zirconium dichloride.

6. The process of claim 3 wherein said aprotic, polar solvent is tetrahydrofuran.

7. The process of claim 1 wherein said slurry is heated at reflux temperature.

8. A process for the purification of impure metallocene that contains at least a tetrahydrofuran-containing impurity, which process comprises refluxing a slurry of said metallocene at elevated temperature in tetrahydrofuran solvent, the amount of the tetrahydrofuran solvent relative to said metallocene being such that there are at least 7 milliliters of tetrahydrofuran per gram of said impure metallocene, and the duration of the refluxing being sufficient to extract impurities including tetrahydrofuran-containing impurity from said metallocene into said solvent such that the amount of said tetrahydrofuran-containing impurity in said metallocene is reduced by at least fifty-five percent; and then separating the impurity-containing solvent from said metallocene.

9. The process of claim 8 wherein said metallocene is an ansa-metallocene.

10. The process of claim 9 wherein said ansa-metallocene is a silicon bridged bis(2-methyl-1-indenyl) ligand-containing metallocene.

11. The process of claim 10 wherein said ansa-metallocene is dimethylsilylbis(2-methyl-1-indenyl) zirconium dichloride, wherein the duration of said heating is in the range of 2 to 17 hours, and wherein the amount of said tetrahydrofuran-containing impurity remaining in said dimethylsilylbis(2-methyl-1-indenyl)zirconium dichloride is no more than 6 mole percent.

* * * * *